United States Patent
Fukui et al.

(10) Patent No.: US 10,825,175 B2
(45) Date of Patent: Nov. 3, 2020

(54) APPARATUS, METHOD, AND MEDIUM FOR REDUCING PIXEL VALUES IN UNNECESSARY REGIONS IN MEDICAL IMAGES

(71) Applicant: CANON KABUSHIKI KAISHA, Tokyo (JP)

(72) Inventors: Toshifumi Fukui, Yokohama (JP); Yohei Hashizume, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1 day.

(21) Appl. No.: 16/190,718

(22) Filed: Nov. 14, 2018

(65) Prior Publication Data

US 2019/0164284 A1    May 30, 2019

(30) Foreign Application Priority Data

Nov. 28, 2017    (JP) .................................. 2017-228149

(51) Int. Cl.
*G06T 7/00* (2017.01)
*G06T 11/60* (2006.01)
*A61B 5/00* (2006.01)
*A61B 5/145* (2006.01)
*G06T 5/50* (2006.01)
*G06T 5/40* (2006.01)
*G06T 5/00* (2006.01)

(52) U.S. Cl.
CPC ............ *G06T 7/0014* (2013.01); *A61B 5/004* (2013.01); *A61B 5/14542* (2013.01); *G06T 5/002* (2013.01); *G06T 5/40* (2013.01); *G06T 5/50* (2013.01); *G06T 11/60* (2013.01); *A61B 5/0095* (2013.01); *A61B 5/4312* (2013.01); *G06T 2200/24* (2013.01); *G06T 2207/10132* (2013.01); *G06T 2207/30068* (2013.01); *G06T 2207/30088* (2013.01); *G06T 2207/30101* (2013.01)

(58) Field of Classification Search
None
See application file for complete search history.

(56) References Cited

U.S. PATENT DOCUMENTS 6,711,293 B1    3/2004    Lowe
9,767,557 B1 *  9/2017    Gulsun ................. G06T 7/0012
(Continued)

FOREIGN PATENT DOCUMENTS

JP    2013-188461 A    9/2013

*Primary Examiner* — Steven Z Elbinger
(74) *Attorney, Agent, or Firm* — Canon U.S.A., Inc. I.P. Division

(57) ABSTRACT

An image processing apparatus acquires a plurality of pieces of first image data generated using volume data that is based on acoustic waves, extracts feature points from a plurality of pieces of the first image data, sets an unnecessary region to one or a plurality of pieces of the first image data using a distribution of the extracted feature points, reduces pixel values of the unnecessary region in one or a plurality of pieces of the first image data to which the unnecessary region has been set, and generates second image data using one or a plurality of pieces of the first image data in which the pixel values of the unnecessary region have been reduced and one or a plurality of pieces of the first image data in which the unnecessary region is not included.

12 Claims, 15 Drawing Sheets

(56) References Cited

U.S. PATENT DOCUMENTS

| | | | |
|---|---|---|---|
| 2004/0057608 A1* | 3/2004 | Souluer | A61B 5/0053 382/128 |
| 2006/0269111 A1* | 11/2006 | Stoecker | G06F 19/321 382/128 |
| 2013/0245426 A1* | 9/2013 | Lee | A61B 6/502 600/411 |
| 2014/0135622 A1* | 5/2014 | Ohi | A61B 6/022 600/425 |
| 2015/0054826 A1* | 2/2015 | Varga | F41G 3/04 345/421 |
| 2016/0055650 A1* | 2/2016 | Park | G06T 19/20 382/131 |
| 2016/0100760 A1* | 4/2016 | Ryu | A61B 6/5247 600/414 |
| 2016/0203600 A1* | 7/2016 | Abdolell | A61B 6/502 382/132 |
| 2018/0075590 A1* | 3/2018 | Yamasaki | H04N 5/765 |
| 2018/0214072 A1* | 8/2018 | Zingaretti | A61B 5/448 |

* cited by examiner

FIG.2A
FIG.2B
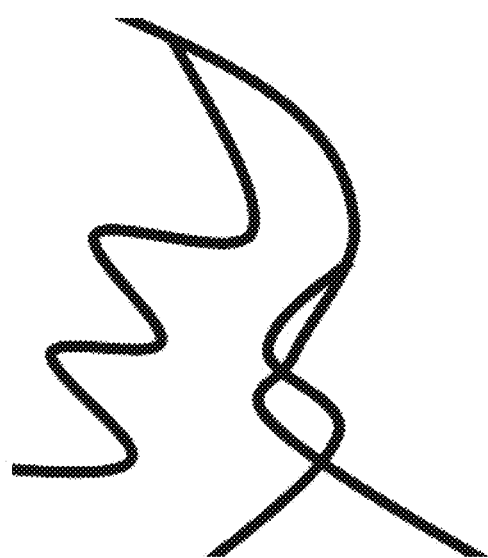
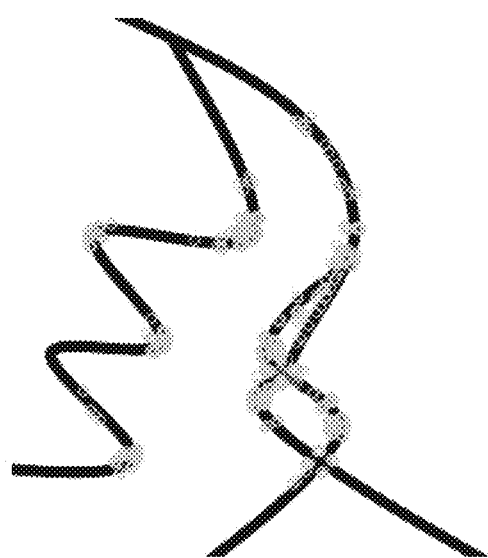

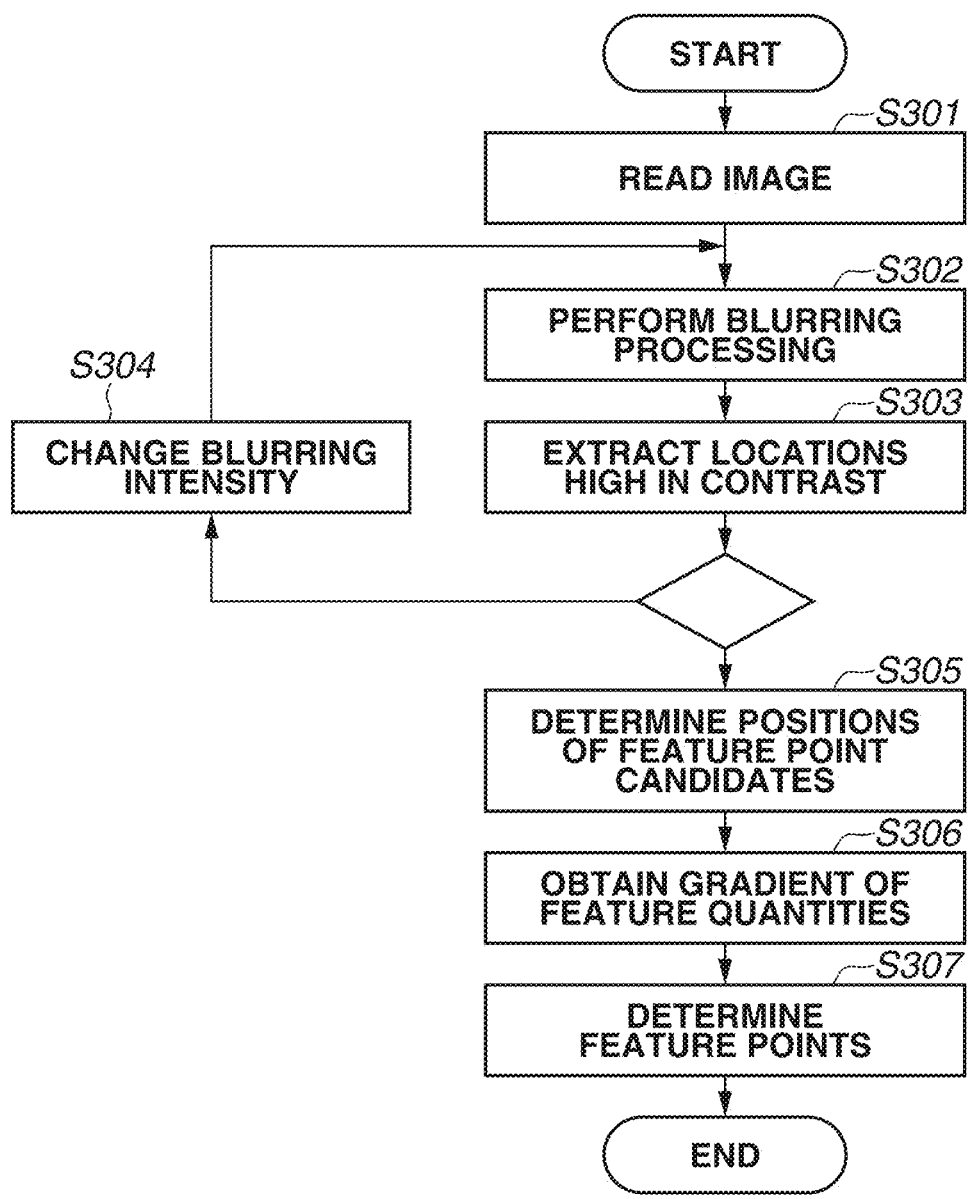

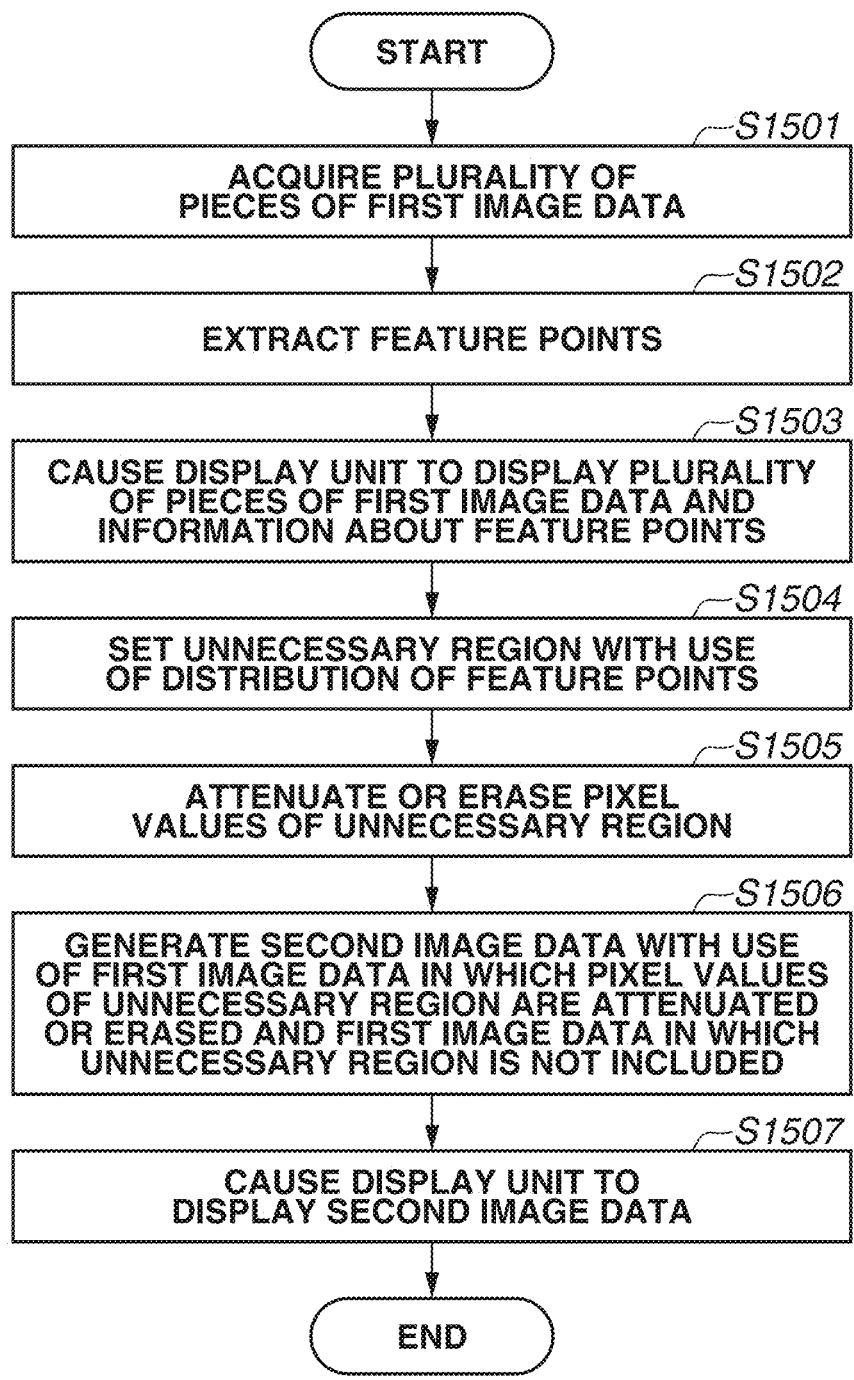

APPARATUS, METHOD, AND MEDIUM FOR REDUCING PIXEL VALUES IN UNNECESSARY REGIONS IN MEDICAL IMAGES

BACKGROUND

Field

Aspects of the present disclosure generally relate to an image processing apparatus, an image processing method, and a non-transitory computer-readable storage medium.

Description of the Related Art

Photoacoustic imaging can be implemented by an imaging apparatus that receives acoustic waves generated from an optical absorber irradiated with light and then images a spatial distribution of the optical absorber. Applying photoacoustic imaging to biological objects enables non-invasively performing vascular imaging.

It is known that photoacoustic imaging apparatuses have an issue where photoacoustic waves generated from a skin surface make it difficult for a signal derived from a site of interest inside the biological object to be made visible.

Japanese Patent Application Laid-Open No. 2013-188461 discusses a method of detecting a skin area based on the signal intensity of photoacoustic waves and then reducing the signal intensity of an area around the skin area.

When image capturing is performed on a breast by a photoacoustic imaging apparatus, strong signals derived from not only the skin surface but also the nipple and areola are detected. Such strong signals derived from the nipple and its surrounding tissues become unnecessary signals with respect to the purpose of visualizing a blood vessel. In the case of using a method discussed in Japanese Patent Application Laid-Open No. 2013-188461, only a signal derived from the nipple present on the skin surface can be reduced, but, actually, an unnecessary region also exists at a position somewhat deeper than the skin. To reduce this unnecessary signal, a method of uniformly widening a range to be determined as a skin and surrounding region can be conceived, but a signal derived from an essential region of interest may also be additionally reduced.

SUMMARY

The present disclosure is directed to improving the visibility of image data by reducing the visibility of an unnecessary region.

According to an aspect of the present invention, an image processing apparatus includes an acquisition unit configured to acquire a plurality of pieces of first image data generated using volume data that is based on acoustic waves, an extraction unit configured to extract feature points from a plurality of pieces of the first image data, a setting unit configured to set an unnecessary region to one or a plurality of pieces of the first image data using a distribution of the extracted feature points, an image processing unit configured to reduce pixel values of the unnecessary region in one or a plurality of pieces of the first image data to which the unnecessary region has been set, and a generation unit configured to generate second image data using one or a plurality of pieces of the first image data in which the pixel values of the unnecessary region have been reduced and one or a plurality of pieces of the first image data in which the unnecessary region is not included.

Further features will become apparent from the following description of exemplary embodiments with reference to the attached drawings.

BRIEF DESCRIPTION OF THE DRAWINGS

FIGS. 2A and 2B are diagrams illustrating examples of local feature quantities on an image, which are acquired by a general method of image processing.

FIG. 3 is a flowchart illustrating an example of a processing procedure for a general method concerning detection of local feature quantities of an image.

FIG. 15 is a flowchart illustrating a processing procedure in a third exemplary embodiment.

DESCRIPTION OF THE EMBODIMENTS

Figure 1A:
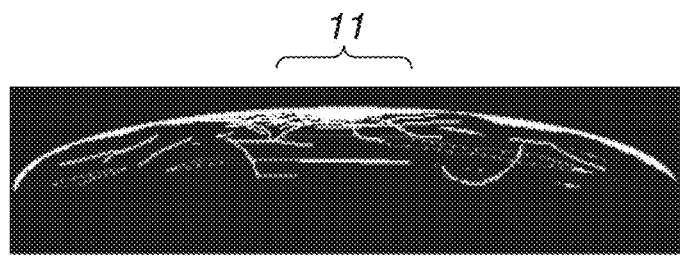
FIGS. 1A and 1B are diagrams illustrating examples of images obtained at the axial plane cross-section and the coronal plane cross-section after volume data is acquired by capturing an image of a breast with a photoacoustic imaging apparatus.

FIG. 1A is a diagram illustrating an image obtained at the axial plane cross-section after volume data is acquired by capturing an image of a breast with a photoacoustic imaging apparatus.

When photoacoustic imaging is performed on a breast by irradiating the breast with light of wavelengths that are greatly absorbed by hemoglobin, an image can be generated from photoacoustic waves derived from hemoglobin. This enables visualizing blood vessels in the breast.

Most of photoacoustic waves acquired by irradiating a biological object with light are derived from optical absorption in hemoglobin in blood vessels. However, since melanin pigments in tissues under the skin have the property of non-specific optical absorption in part, photoacoustic waves are also generated from, for example, moles or hairs. In a case where photoacoustic imaging is performed for a breast, photoacoustic waves derived from the nipple and areola are also additionally generated and then become a noise source at the time of imaging.

Figure 1B:
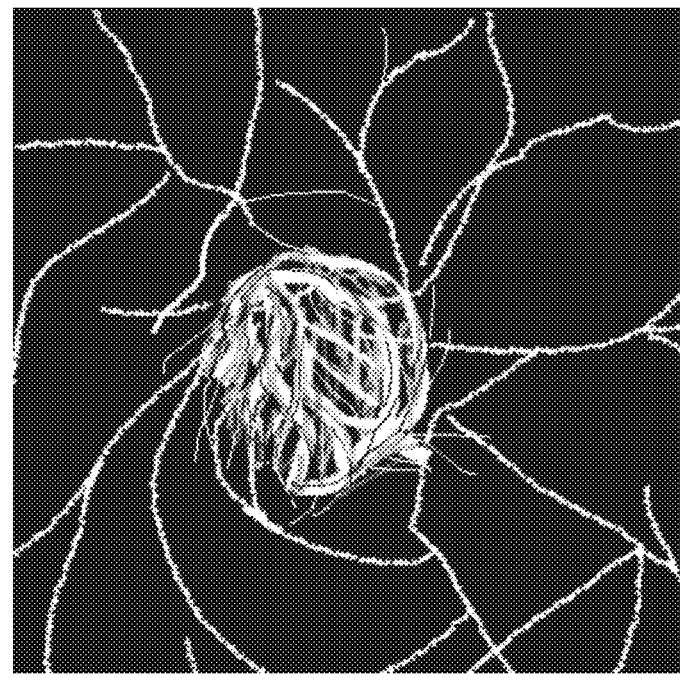

A region indicated by reference character "11" in FIG. 1A represents a region in which an image is generated from a signal derived from the nipple. In the vicinity of the region indicated by reference character "11" in FIG. 1A, there are many signals derived from the nipple and areola, so that it is hard to recognize the presence or absence of signals derived from surrounding blood vessels. As illustrated in FIG. 1B, in a case where an image is generated at the coronal plane cross-section by a maximum intensity projection (MIP) method, such an effect is particularly conspicuous.

Since the nipple and areola are tissues near the skin surface, removing signals derived from portions near the skin surface based on the method discussed in Japanese Patent Application Laid-Open No. 2013-188461 enables erasing a certain amount of signals. However, the method discussed in Japanese Patent Application Laid-Open No. 2013-188461 is a method of uniformly removing signals derived from portions of the skin surface and is, therefore, not able to remove signals derived from the nipple and areola at positions somewhat deeper than the skin surface. It is also difficult to remove only signals derived from portions near the nipple and areola at positions near the skin surface.

Therefore, in view of the above issues, the present inventors devised a method of, when visualizing signals derived from blood vessels in a region of interest, extracting a photoacoustic signal derived from a nipple and areola portion and distinguishing this photoacoustic signal from photoacoustic signals derived from other regions.

Hereinafter, a method of distinguishing a photoacoustic signal derived from a nipple and areola portion from photoacoustic signals derived from other regions according to the present disclosure is described with reference to the drawings.

Prior to description of each exemplary embodiment, a method of image processing for extracting local feature quantities on an image, which is performed in each exemplary embodiment, is described. FIGS. 2A and 2B are diagrams illustrating examples of local feature quantities on an image, which are acquired by a general method of image processing. The image illustrated in FIG. 2B is obtained by performing feature quantity extraction processing on the image illustrated in FIG. 2A and superimposing and displaying portions having large feature quantities thereon.

A general method concerning detection of local feature quantities on an image is described based on U.S. Pat. No. 6,711,293 with reference to the flowchart of FIG. 3. While each processing operation in the following description is assumed to be performed by a control unit included in the image processing apparatus, this is merely an example, and the following description is not limited to this. Moreover, the method concerning detection of local feature quantities on an image is not limited to the following method.

First, in step S301 in FIG. 3, the control unit reads an image serving as a target. If the image serving as a target is a color image, the control unit converts the color image into a gray scale image when reading the image.

Next, in step S302, the control unit performs blurring processing on the image, and, in step S303, the control unit extracts locations which are high in contrast from the image subjected to blurring processing. In step S304, the control unit changes the blurring intensity, and then repeats step S302 and step S303.

After repeating steps S302, S303, and S304 a specified number of times, in step S305, the control unit extracts pixels robust over scale changes as feature point candidates. The control unit selects, as feature point candidates, locations in which not only the contrast intensity is strong, but also changes in pixel value with respect to all directions are observed.

Next, in step S306, the control unit obtains a gradient of intensities of pixel values using pixel values of pixels determined as feature point candidates and their surrounding pixels. The control unit sets, as an observation region, pixels serving as feature point candidates and their surrounding pixels, combines an image of the observation region and a blurring image obtained from that image, and calculates a gradient of pixel values and a frequency for each angle of the gradient. This frequency information is expressed with vectors to represent local feature quantities of an image, and, in step S307, the control unit determines, as feature points, points having local feature quantities greater than or equal to an optionally designated threshold value.

The above-described method enables extracting feature points having local feature quantities that are robust over enlargement, reduction, rotation, and luminance change on an image.

Next, a photoacoustic apparatus in each exemplary embodiment is described.

A photoacoustic apparatus according to the present disclosure is an apparatus utilizing a photoacoustic effect that receives acoustic waves generated inside a subject by irradiating the subject with light (electromagnetic waves) and then acquires characteristic information about the subject as image data. In this case, the characteristic information is information about characteristic values respectively corresponding to a plurality of positions inside a subject, which are generated from received signals acquired by receiving photoacoustic waves.

Characteristic information acquired by photoacoustic measurement is a value in which the absorption rate of light energy is reflected. For example, the characteristic information includes a generation source of acoustic waves generated by light irradiation, an initial sound pressure inside a subject, a light energy absorption density or absorption coefficient derived from the initial sound pressure, and the concentration of a substance constituting a tissue.

Spectral information such as the density of a substance constituting a subject is acquired based on photoacoustic waves generated by light of a plurality of different wavelengths. The spectral information can be an oxygen saturation, a value obtained by adding the weight of an intensity such as an absorption coefficient to the oxygen saturation, a total hemoglobin concentration, an oxyhemoglobin concentration, or a deoxyhemoglobin concentration. The spectral information can be a glucose concentration, a collagen concentration, a melanin concentration, or a volume fraction of fat or water.

Each exemplary embodiment described below is directed to a photoacoustic imaging apparatus that irradiates a subject with light of wavelengths adapted for hemoglobin serving as an absorber and thus acquires data about the distribution and shape of blood vessels inside the subject and data about an oxygen saturation distribution in the blood vessels, thus generating an image thereof.

A two-dimensional or three-dimensional characteristic information distribution is acquired based on characteristic information at each position inside the subject. Distribution data can be generated as image data. The characteristic information can be obtained not as numerical data, but as distribution information at each position inside the subject. In other words, the characteristic information is distribution information such as an initial sound pressure distribution, an energy absorption density distribution, an absorption coefficient distribution, or an oxygen saturation distribution.

Acoustic waves in the present specification are typically ultrasonic waves, and include elastic waves called sound waves or photoacoustic waves. An electrical signal into which acoustic waves are converted by, for example, a probe is also referred to as an "acoustic signal". However, the term "ultrasonic waves" or "acoustic waves" in the present specification is not intended to limit the wavelengths of such elastic waves. Acoustic waves generated by a photoacoustic effect are referred to as "photoacoustic waves" or "photoultrasonic waves". An electrical signal derived from photoacoustic waves is also referred to as a "photoacoustic signal". In the present specification, the photoacoustic signal is a concept including both an analog signal and a digital signal. The distribution data is also referred to as "photoacoustic image data" or "reconstructed image data".

The principle of photoacoustic imaging is described with reference to FIG. 4.

Figure 4:
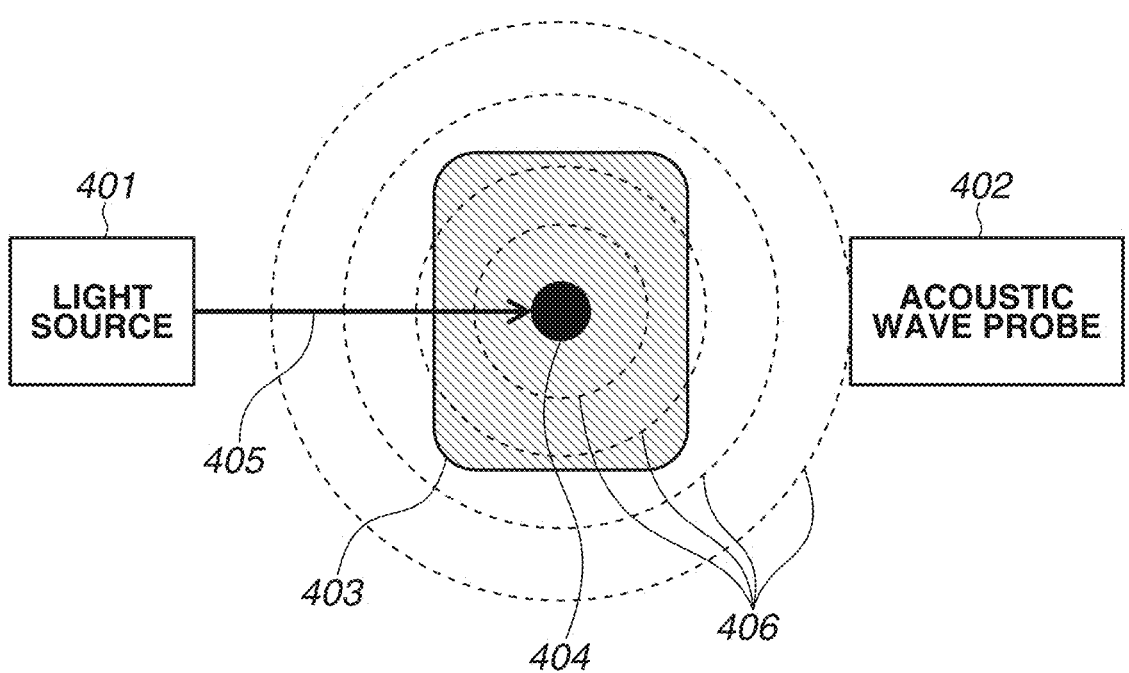
FIG. 4 is a diagram used to describe the principle of photoacoustic imaging.

FIG. 4 illustrates a light source 401, an acoustic wave probe 402, a subject 403, an optical absorber 404 existing inside the subject 403, light 405 radiated from the light source 401, and acoustic waves 406 emitted from the optical absorber 404.

When the light 405 is radiated from the light source 401 onto the subject 403, the light 405 reaches the inside of the subject 403 and is then absorbed by the optical absorber 404. In this case, the acoustic waves 406 are generated and then reach the acoustic wave probe 402. The acoustic waves 406 received by the acoustic wave probe 402 are converted into electrical signals and are then made into an image by an arithmetic operation that is based on, for example, radiation timing of light and the propagation velocity in the subject, and the image is displayed on a screen.

In a case where hemoglobin in red blood cells is targeted as the optical absorber 404, light of such wavelengths as to be specifically absorbed by hemoglobin is radiated. An image that would be obtained by this radiation represents hemoglobin locally existing in a biological object. Since a great amount of hemoglobin exists in red blood cells, this enables acquiring an image of the blood vessel in which red blood cells exist.

Figure 5:
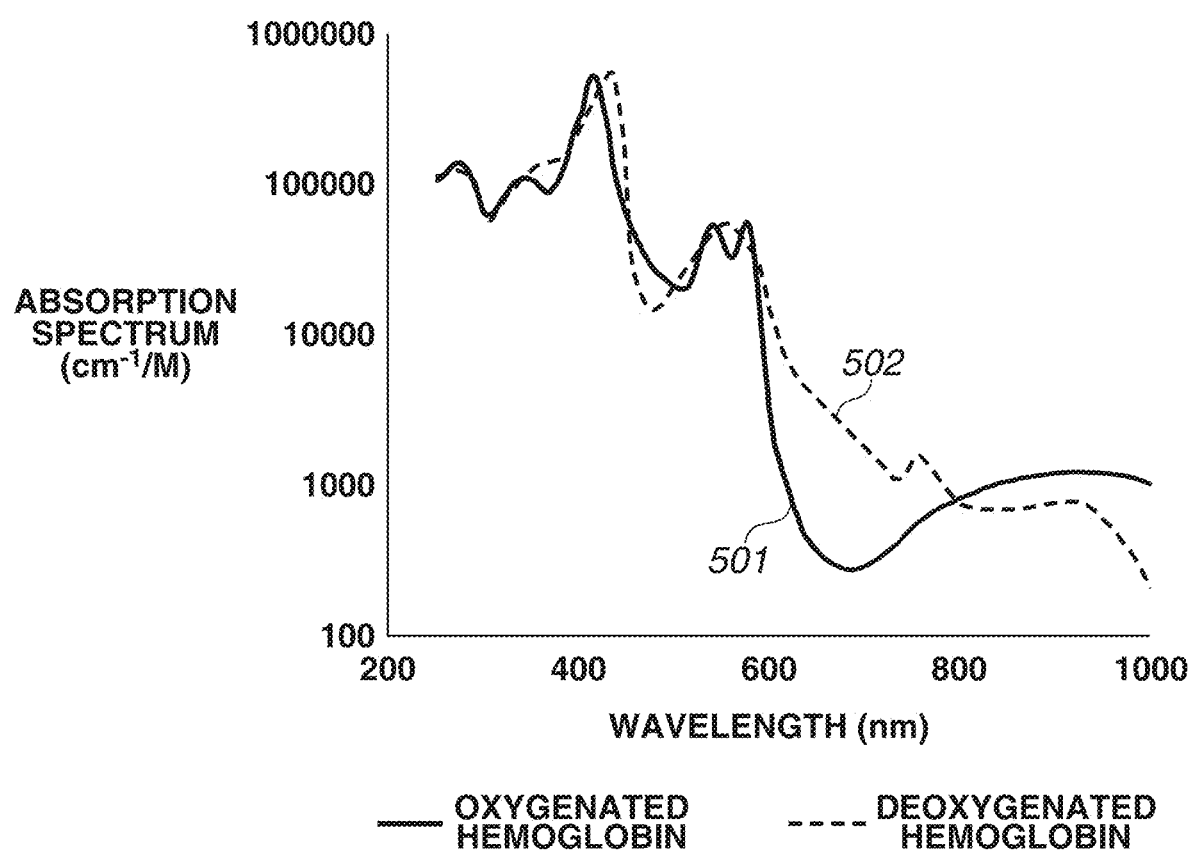
FIG. 5 is a diagram illustrating an example of a graph of absorption spectra of oxygenated hemoglobin and deoxygenated hemoglobin.

FIG. 5 is a graph illustrating optical absorption spectra of oxygenated hemoglobin and deoxygenated hemoglobin. The horizontal axis of the graph indicates wavelength (nanometer (nm)), and the vertical axis of the graph indicates absorption spectrum ($cm^{-1}/M$). In this graph, a solid line denoted by reference numeral 501 represents an absorption spectrum of oxygenated hemoglobin, and a dashed line denoted by reference numeral 502 represents an absorption spectrum of deoxygenated hemoglobin. Irradiating a subject with light of wavelengths in which there are large differences in absorption spectrum between oxygenated hemoglobin and deoxygenated hemoglobin and analyzing acoustic waves acquired by such irradiation enable acquiring an abundance ratio between oxygenated hemoglobin and deoxygenated hemoglobin in the subject.

Hereinafter, a configuration of the photoacoustic apparatus according to a first exemplary embodiment is described with reference to FIG. 6. Furthermore, the configuration of the photoacoustic apparatus which is described as follows is merely an example, and the present exemplary embodiment is not limited to this configuration.

Figure 6:
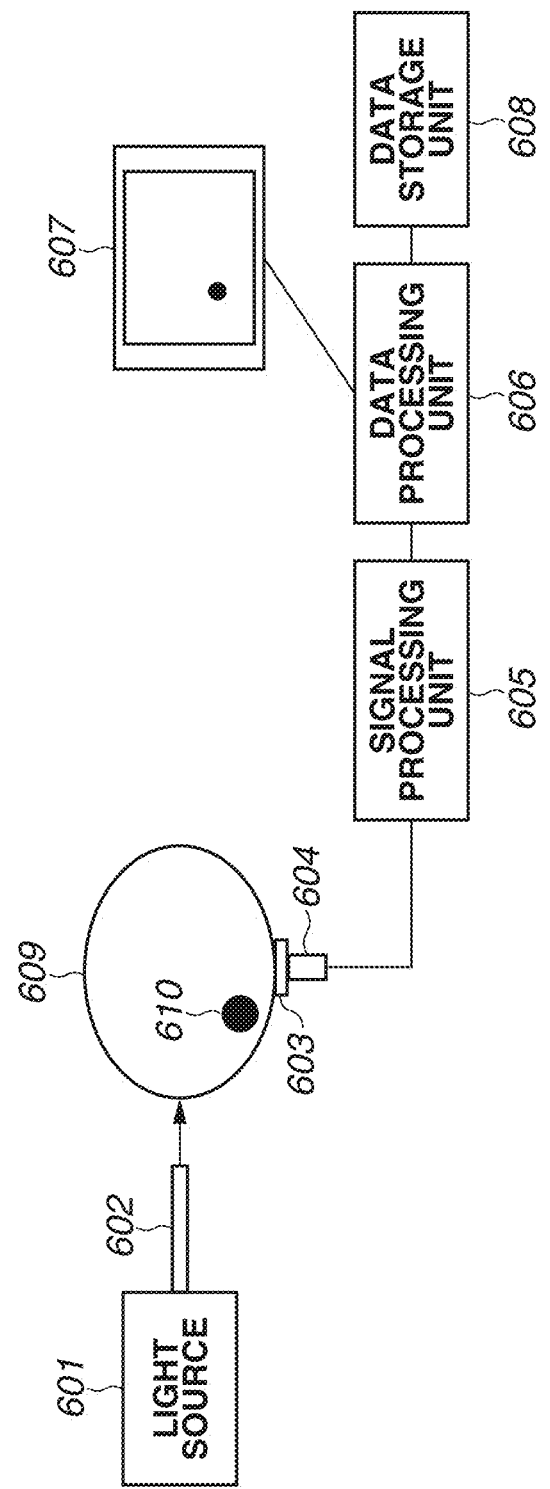
FIG. 6 is a diagram illustrating an example of a configuration of a photoacoustic apparatus.

The photoacoustic apparatus illustrated in FIG. 6 is configured to include a light source 601, an optical system 602, an acoustic matching material 603, an acoustic wave probe 604, a signal processing unit 605, a data processing unit 606, and a display unit 607. A data storage unit 608 is connected to the data processing unit 606 via a bus or a network. Reference numeral 609 denotes a subject, and reference numeral 610 denotes an optical absorber present inside the subject.

The light source 601 is a device that generates pulsed light with which to irradiate the subject. While it is desirable that the light source be a laser light source to obtain significant power, a light-emitting diode or a flash lamp can also be used instead of a laser. In a case where a laser is used as the light source, various lasers, such as a solid-state laser, a gas laser, a dye laser, and a semiconductor laser, can be used.

It is desirable that the wavelength of pulsed light be a specific wavelength that is absorbed by a specific component from among components constituting the subject and a wavelength the light of which is propagated to the inside of the subject. Specifically, it is desirable that the wavelength be 700 nanometers (nm) or more and 1,200 nm or less. Light of this wavelength region can reach a relatively deep portion of the biological object, so that information about the deep portion can be acquired.

To cause photoacoustic waves to be effectively generated, it is necessary to radiate light in a sufficiently short amount of time based on a thermal property of the subject. In a case where the subject is a biological object as illustrated in the present exemplary embodiment, it is favorable that the pulse width of pulsed light that is generated from the light source is several tens of nanoseconds or less.

For example, the timing, waveform, and intensity of light irradiation are controlled by a control unit (not illustrated).

The optical system 602 is a member which transmits pulsed light emitted from the light source 601. The light emitted from the light source 601 is guided to and radiated onto the subject while being processed into a predetermined light distribution shape by optical components, such as a lens and a mirror. For example, a light waveguide such as an optical fiber can be used to propagate light.

The optical system 602 can include, for example, optical devices, such as a lens, a mirror, a prism, an optical fiber, a diffusing plate, a shutter, and a filter. Any optical components can be used as the optical system 602 as long as they are able to irradiate the subject 609 with light emitted from the light source 601 and processed into a desired shape. Spreading light to a certain degree of area is more desirable than condensing light with a lens in terms of safety of a biological object and broadening of a diagnosis domain.

The acoustic wave probe 604 is a unit that receives acoustic waves coming from the inside of the subject 609 and converts the acoustic waves into an analog electrical signal. The acoustic wave probe is also called a probe, an acoustic wave detection element, an acoustic wave detector, an acoustic wave receiver, or a transducer. Since acoustic waves generated from a biological object are ultrasonic waves of 100 kilohertz (kHz) to 100 megahertz (MHz), an element that can receive the above-mentioned frequency band is used as the acoustic wave probe. Specifically, for example, a transducer utilizing a piezoelectric phenomenon, a transducer utilizing optical resonances, or a transducer utilizing changes in capacity can be used.

It is desirable that acoustic elements that are high in sensitivity and wide in frequency band be used. Specifically, examples of the acoustic element include a piezoelectric element using, for example, piezoelectric zirconate titanate (PZT), a polymer piezoelectric film material such as polyvinylidene fluoride (PVDF), a capacitive micromachined ultrasonic transducer (CMUT), and a Fabry-Perot interferometer. However, the acoustic wave probe is not limited to only the above-cited ones, but can be any type of probe as long as it satisfies the function of a probe.

The acoustic matching material 603, which is a member to match acoustic impedances, is located between the acoustic wave probe 604 and the subject 609. For example, gel, water, or oil can be used as the acoustic matching material 603.

The signal processing unit 605 is a unit that amplifies and converts the acquired analog electrical signal into a digital signal. The signal processing unit 605 can be configured to include an amplifier, which amplifies the received signal, an analog-to-digital (A/D) converter, which performs digital conversion of the analog received signal, a memory such as a first-in first-out (FIFO) memory, which stores the received signal, or an arithmetic circuit such as a field-programmable gate array (FPGA) chip. The signal processing unit 605 can be configured with a plurality of processors or arithmetic circuits.

The data processing unit 606 is a unit that generates subject information, such as an optical absorption coefficient or oxygen saturation in the inside of the subject, based on a digitally-converted photoacoustic signal. Specifically, the data processing unit 606 generates an initial sound pressure distribution in the three-dimensional inside of the subject based on the acquired photoacoustic signal. For example, a universal back projection (UBP) algorithm or a delay and sum algorithm can be used for generation of the initial sound pressure distribution.

The data processing unit 606 generates a three-dimensional light-intensity distribution in the inside of the subject based on the light amount of light with which the subject 609 is irradiated. The three-dimensional light-intensity distribution can be acquired by solving a light diffusion equation based on information about two-dimensional light-intensity distributions.

In addition, the data processing unit 606 has, for example, the function of generating a three-dimensional absorption coefficient distribution based on the initial sound pressure distribution and the light-intensity distribution and the function of generating an oxygen saturation distribution from an absorption coefficient distribution generated based on light of a plurality of wavelengths.

The data processing unit 606 can be configured with a computer (image processing apparatus) that includes a central processing unit (CPU), a random access memory (RAM), a non-volatile memory, and a control port. Control is performed by a program stored in at least one non-volatile memory being executed by at least one CPU. The data processing unit 606 can be implemented by a general-purpose computer or an exclusively designed workstation. Units that bear the arithmetic operation function of the data processing unit 606 can be configured with a processor, such as a CPU or a graphics processing unit (GPU), or an arithmetic circuit, such as an FPGA chip. These units are not only configured with a single processor or arithmetic circuit, but also can be configured with a plurality of processors or arithmetic circuits.

Units that bear the storage function of the data processing unit 606 can be a non-transitory storage medium, such as a read-only memory (ROM), a magnetic disc, or a flash memory, or a volatile medium, such as a RAM. A storage medium in which a program is stored is a non-transitory storage medium. These units are not only configured with a single storage medium, but also can be configured with a plurality of storage media. Units that bear the control function of the data processing unit 606 is configured with an arithmetic element such as a CPU.

The display unit 607 is a unit that displays information acquired by the data processing unit 606 and information processed thereby, and is typically a display device. The display unit 607 can be provided with a plurality of display sections and can perform parallel display.

The data storage unit 608 is a storage unit configured with, for example, a magnetic disc, and is connected to the data processing unit 606 via an internal bus or a network.

The subject 609 does not constitute a part of the photoacoustic imaging apparatus, but is described as follows. The photoacoustic imaging apparatus according to the present exemplary embodiment is an apparatus that visualizes, as an image, the state of the inside of the body, such as a site within a human or animal that may be diseased. While a biological object, such as, for example, a breast, a limb, or a finger, can be the subject, a breast is assumed in the present exemplary embodiment.

Since the inside of a breast has blood vessels running therein and contains optical absorbers 610 having large optical absorption coefficients, such as oxygenated hemoglobin and deoxygenated hemoglobin, photoacoustic waves are generated therefrom due to light irradiation. The hemoglobin distribution in the breast is visualized by reconstructing the generated photoacoustic waves as an image. Since hemoglobin is present mainly in red blood cells and the red blood cells are present in blood vessels, a structure of the blood vessels is visualized as an image. When light of a plurality of wavelengths is used for irradiation, an abundance ratio between oxygenated hemoglobin and deoxygenated hemoglobin can also be visualized.

<Outline of Measurement>

Next, a method in which the photoacoustic apparatus according to the present exemplary embodiment measures a biological object serving as a subject is described.

First, pulsed light emitted from the light source 601 is radiated onto the subject 609 via the optical system 602. When a part of energy of light propagated inside the subject 609 is absorbed by the optical absorber 610, such as blood, acoustic waves are generated from the optical absorber 610 due to thermal expansion. If cancer is present in the biological object, light is specifically absorbed in new blood vessels of the cancer in a similar way to blood in other normal sites, so that acoustic waves are generated from the new blood vessels. Photoacoustic waves generated in the inside of the biological object are received by the acoustic wave probe 604.

The signal received by the acoustic wave probe 604 is converted by the signal processing unit 605 and is then analyzed by the data processing unit 606. A result of the analysis becomes volume data representing characteristic information about the inside of the biological object (for example, an initial sound pressure distribution or an absorption coefficient distribution) (hereinafter referred to as "photoacoustic data"), the volume data is converted into a two-dimensional image, and, then, the two-dimensional image is output via the display unit 607.

The photoacoustic data, which has been derived from the optical absorber 610 and has then been converted into data by the data processing unit 606, is then stored in the data storage unit 608. At this time, information about the subject or other pieces of information about measurement can be associated with the photoacoustic data. Data to be stored in the data storage unit 608 includes, for example, volume data obtained by measurement, image data, information about a subject, and parameters used at the time of image capturing.

While it is favorable that photoacoustic data to be stored in the data storage unit 608 is three-dimensional volume data, two-dimensional image data obtained from the photoacoustic data can be stored in the data storage unit 608. For example, two-dimensional data obtained by a maximum intensity projection (MIP) method from three-dimensional data can be stored or a two-dimensional image obtained by clipping three-dimensional data with any optional flat surface or curved surface can be stored.

<Display of Subject Image>

Figure 7:
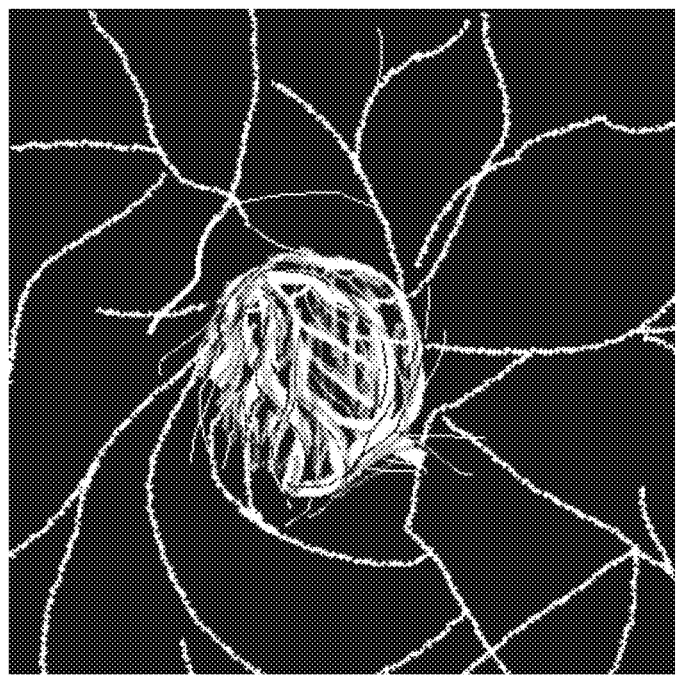
FIG. 7 is a diagram illustrating an example of a subject image acquired by performing photoacoustic measurement with a breast used as a subject.

FIG. 7 illustrates an example of a subject image obtained by performing photoacoustic measurement with a breast used as a subject. Specifically, this example is obtained by irradiating the entire breast with light of such wavelengths as to be easily absorbed by hemoglobin, generating volume data based on the acquired acoustic waves, converting the volume data into a two-dimensional image using the maximum intensity projection method, and visualizing the two-dimensional image. The image illustrated in FIG. 7 is an image corresponding to the coronal plane with the observer's eye set in the frontal direction. While, in the description of the present exemplary embodiment, image data on the coronal plane is assumed to be generated, the present exemplary embodiment is not limited to this, but image data on the axial plane or the sagittal plane can be generated according to an intended use or purpose.

An information processing apparatus that targets an image obtained by the photoacoustic apparatus according to the present exemplary embodiment has the function of performing imaging with a breast set as a target while at least reducing a signal derived from a nipple and surrounding region, which is a signal source other than blood vessels, based on an MIP image directed to visualizing blood vessels. Such a function is described with reference to FIG. 8 and FIGS. 9A, 9B, and 9C.

Figure 8:
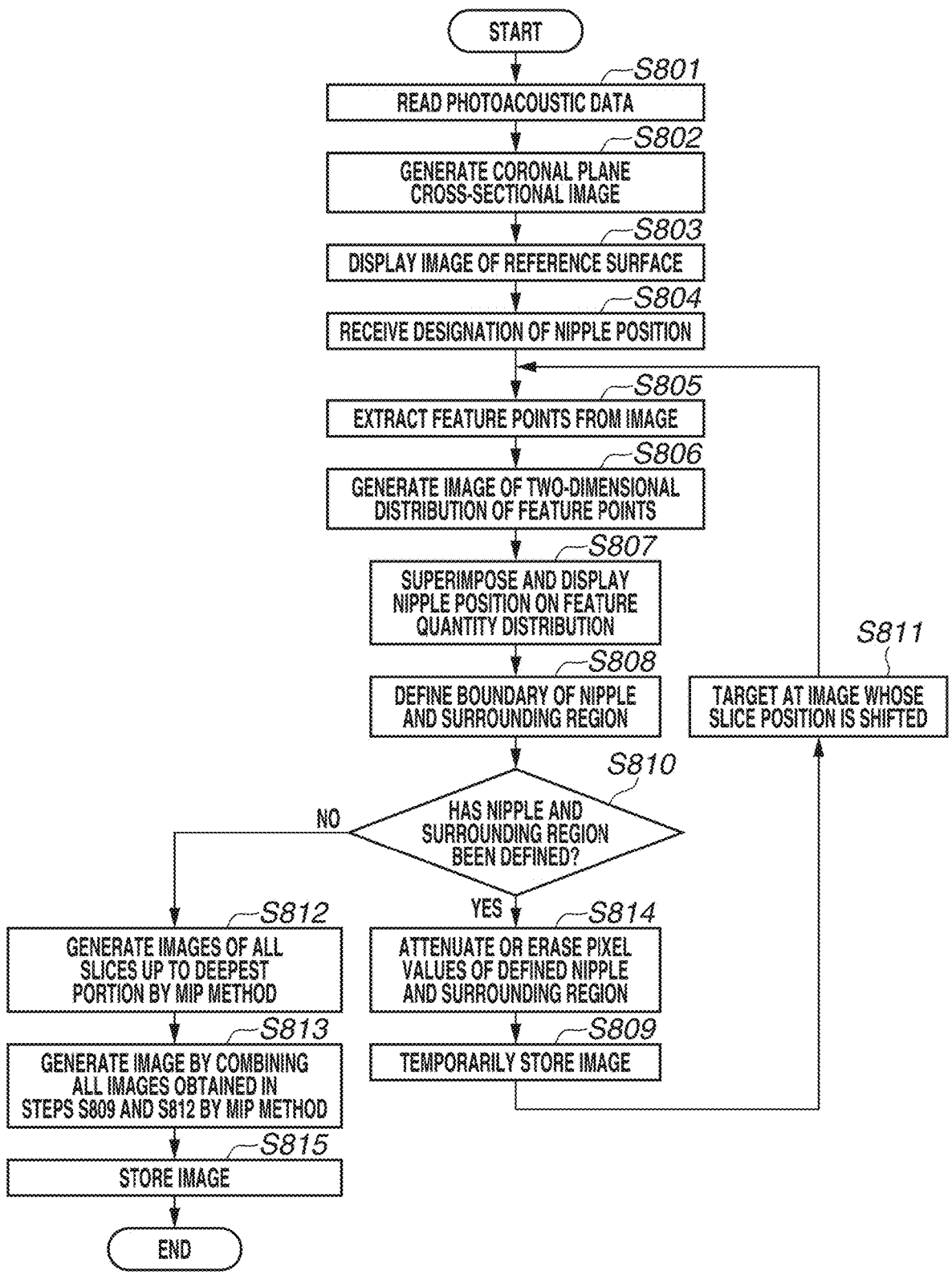
FIG. 8 is a flowchart illustrating an example of a processing procedure for acquiring the image of a breast by a maximum intensity projection method in a state in which a signal derived from a nipple and surrounding region is reduced.

FIG. 8 is a flowchart for obtaining an image of the breast by the maximum intensity projection method in a state in which a signal derived from the nipple and surrounding region is reduced.

In step S801, the data processing unit 606 reads photoacoustic data. The photoacoustic data is three-dimensional volume data.

In step S802, the data processing unit 606 generates a coronal plane cross-sectional image from the read photoacoustic data by the maximum intensity projection method. The cross-sectional image generated in this step is a plurality of MIP images obtained by slicing the photoacoustic data with a slice thickness set by the apparatus. At this time, the skin surface of the subject can be detected and an image deformed in such a manner that the detected skin surface becomes a flat surface can be generated. Moreover, a value set by the user can be used as the slice thickness.

In step S803, the data processing unit 606 causes the display unit 607 to display the image of a reference surface from among the images generated in step S802. The reference surface can be any optionally set surface, such as a skin surface, a horizontal surface including the tip of the nipple, or a surface including the origin of a depth axis used by image generation.

In step S804, the data processing unit 606 receives designation of the coordinates of the nipple on the displayed image of the skin surface. This step can be omitted. The designation of the nipple position by the user can be performed using a pointing device such as a mouse or can be performed with the coordinates being input using numerical values. A captured image obtained by, for example, performing image capturing at the same time as the acquisition of photoacoustic data can be used.

When the nipple and its surrounding region are defined as an unnecessary region, since the nipple position is defined as a reference position, the user can determine the unnecessary region while distinguishing the unnecessary region from other sites having large local feature quantities derived from, for example, body hair or a mole on the body surface. However, setting the nipple position as a reference point is not an essential step in the present exemplary embodiment.

In step S805, the data processing unit 606 calculates local feature quantities with respect to the image generated in step S803, for example, based on the flowchart described with reference to FIG. 3, thus extracting feature points. The method of extracting feature points is not limited to this, but various methods, such as a histogram of oriented gradients (HOG) feature extraction method or an oriented FAST and rotated BRIEF (ORB) method, can be used.

In step S806, the data processing unit 606 generates an image of a two-dimensional distribution of the extracted feature points.

In step S807, the data processing unit 606 superimposes the nipple position designated by the user in step S804 on the image of feature points extracted in step S806, and causes the display unit 607 to display the image obtained by superimposition. A graphical user interface (GUI) enabling switching between displaying the image generated in step S806 and the image generated in step S803 can be displayed.

Figure 9A:
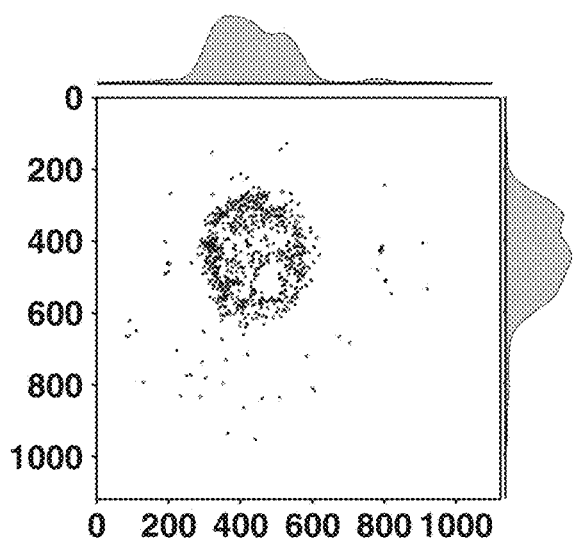
FIGS. 9A, 9B, and 9C are diagrams illustrating examples of screens which are displayed in step S807.
Figure 9B:
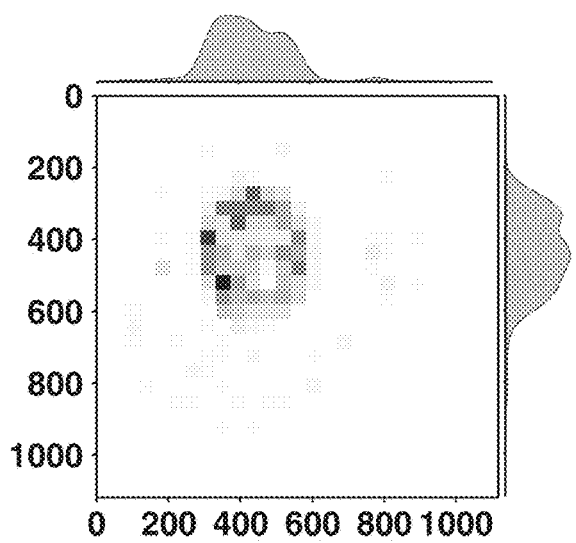
Figure 9C:
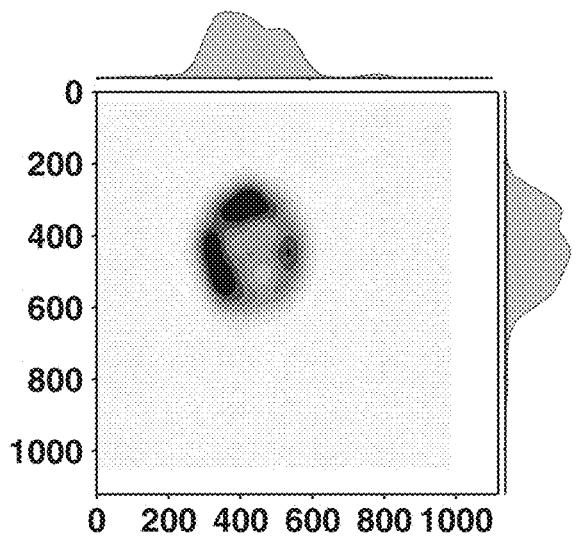

In step S807, the distribution of feature points can be displayed with points as illustrated in FIG. 9A, can be displayed with a two-dimensional histogram as illustrated in FIG. 9B, or can be displayed with an image of the estimated point density as illustrated in FIG. 9C. A configuration in which these display methods can be switched on a GUI can be employed.

In step S808, the data processing unit 606 defines a region having a high distribution density of feature points in the vicinity of the nipple position designated in step S804 as an unnecessary region different from a region of interest.

A specific procedure in step S808 is now described. First, a screen (GUI) illustrated in FIG. 10, which is displayed in step S807, is described.

Figure 10:
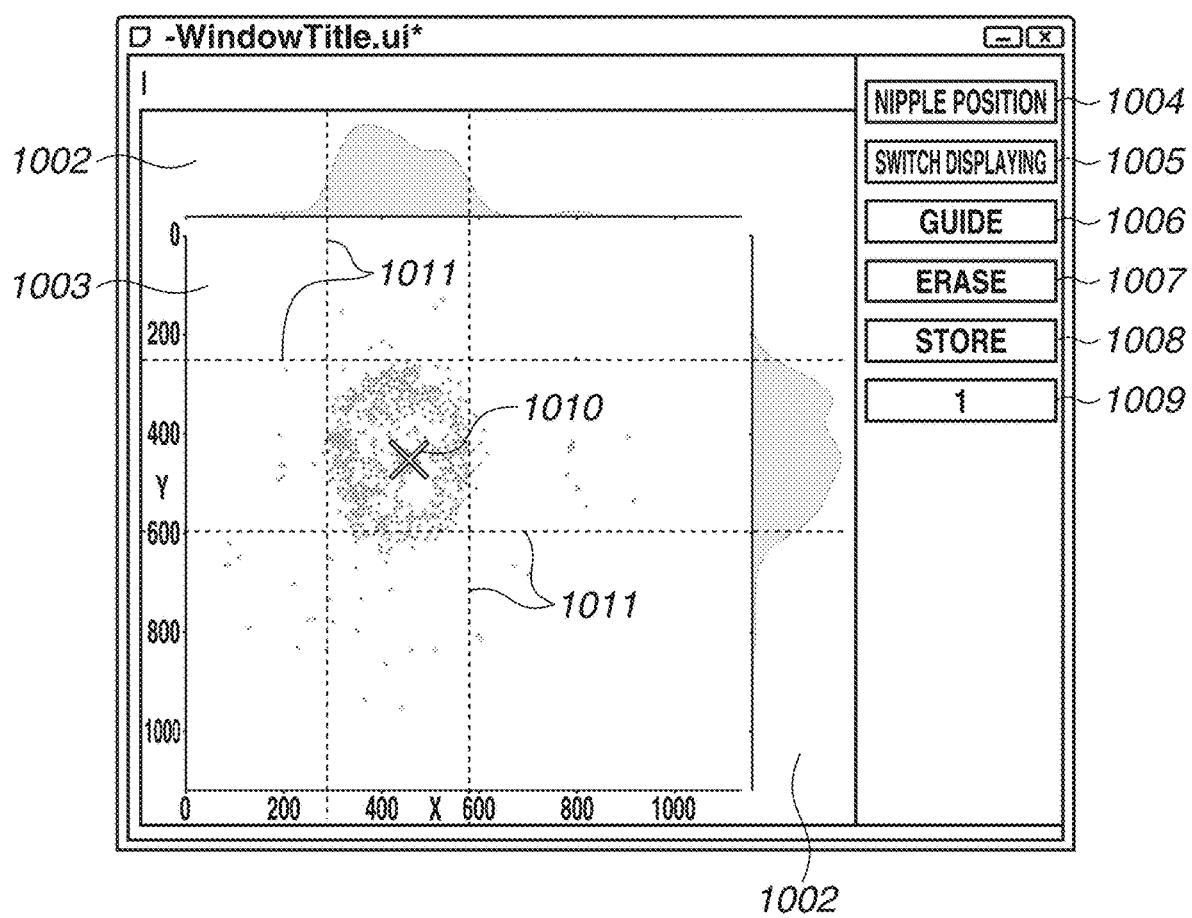
FIG. 10 is a diagram illustrating an example of a graphical user interface (GUI) which is used to define an unnecessary region.

FIG. 10 illustrates an example of a GUI for a method of defining an unnecessary region. A window illustrated in FIG. 10 indicates a runtime image of a computer application having a general GUI. This screen structure is merely an example, and there are various examples of structures according to intended uses or purposes. Therefore, each GUI does not necessarily need to be provided to implement the present exemplary embodiment.

A region 1002 is used to display, in a histogram form, the distribution of feature points extracted by performing step S805 in the flowchart of FIG. 8. Graphs of the histogram form are respectively depicted on the vertical axis and the horizontal axis with respect to an image displayed in a region 1003.

The region 1003 is used to display an image drawn with two-dimensional image data that is based on photoacoustic data. An image to be displayed in this region can be switched for display between forms of information such as those illustrated in FIGS. 9A, 9B, and 9C based on a button 1005 being operated. Thus, the region 1003 is a GUI for switching to another piece of first image data different from a piece of first image data that is being displayed. The user can determine a high signal region derived from the nipple and its surrounding tissues while referring to the information displayed in the region 1003, in which the distribution of feature points is visualized, and the graphs in a histogram form displayed in the region 1002.

Buttons 1004 to 1008 are used for the user to perform respective operations. The button 1004 is used for the user to designate the nipple position on the image displayed in the region 1003 with a pointing device such as a mouse and then finalize the designated position being the nipple position. At this time, the finalized nipple position is displayed in the form of a marker 1010.

The button 1005 is used to switch information to be displayed in the region 1003. This can be implemented by switching with, for example, a radio button or a toggle switch instead of switching with a button.

The button 1006 is used to switch between displaying and non-displaying of guidelines 1011 used to estimate a high-luminance region around the nipple on the region 1003 based on the histograms displayed in the region 1002. This can be in the form of, for example, a pressable button displayed on the window, a radio button or toggle button for switching between displaying and non-displaying, or a menu.

The button 1007 is used to issue an instruction to reduce (attenuate or erase) pixel values of the designated nipple and surrounding region. Both an erasure button and an attenuation button can be located as a GUI, or one of the erasure button and the attenuation button can be located as illustrated in FIG. 10. This can be in the form of, for example, a radio button, a toggle button, or a menu.

The button 1008 is used to issue an instruction to store image data in which pixel values of the nipple and surrounding region have been reduced. When the button 1008 is pressed, the image data is then stored in the data storage unit 608 or a RAM.

An entry field 1009 is used to designate the slice thickness of volume data for performing the maximum intensity projection method. This can be an entry field such as that illustrated in FIG. 10 or can be implemented by inputting with a slide bar or a menu. The slice thickness to be input can be the actual number of slices of an image constituting volume data, or can be implemented by inputting of the actual thickness of tissues in terms of, for example, millimeters.

The marker 1010 indicates the nipple position designated with a pointing device such as a mouse. The color or shape of the marker 1010 differs based on the actual implementation of a program. The nipple position marker 1010 can be set on the distribution screen of feature points such as that illustrated in FIG. 10, or can be displayed in a superimposed manner on the image display region 1003 at the coordinate position matched with the nipple position acquired from the previously captured image at the time of measurement.

The guidelines 1011 are displayed on the region 1003 based on the histograms of feature points displayed in the region 1002. A region surrounded by the guidelines 1011 is indicated as a position around the nipple in which the signal intensity is high. The method of generating the guide lines 1011 includes, for example, a method in which, in a case where the coordinates of the nipple are included in a half-value breadth of the histogram, guidelines are displayed at coordinates at which the frequency has a half value. Alternatively, the outermost outlines of a region in which feature points occurring with frequencies exceeding a threshold value, which the user sets while referring to the histogram shape, are observed can be displayed as the guidelines. The guidelines 1011 can be configured to be able to be switched between displaying and non-displaying with, for example, the button 1006 being operated by the user.

The screen illustrated in FIG. 10 can have the function of designating the slice position with a GUI component such as a slide bar. The slice position for generating image data on a coronal plane can be designated with a GUI component such as a slide bar. The function of designating the slice position can also be implemented by inputting of numerical values of the slice position or selection of the slice position with a menu.

Next, the method of defining an unnecessary region is described. While referring to the histograms of feature points displayed in the region 1002 in the GUI illustrated in FIG. 10, the user designates an unnecessary region using a pointing device such as a mouse. For example, the data processing unit 606 receives an instruction to draw outlines serving as the boundary of an unnecessary region issued using the pointing device, draws the outlines, and then defines a range surrounded by the outlines as an unnecessary region.

Alternatively, as in a third exemplary embodiment described below, an unnecessary region can be automatically discriminated using information about the distribution of feature points. The unnecessary region automatically discriminated can be displayed in a superimposed manner on the region 1003, so that the user is enabled to finely adjust the automatically discriminated unnecessary region using a pointing device such as a mouse.

As described above, the user performs definition of an unnecessary region with respect to image data while referring to, for example, information about the distribution of feature points displayed on a screen or information about a reference point.

In step S810, the data processing unit 606 determines whether an unnecessary region has been defined with respect to image data. In a case where an unnecessary region has been drawn on an image represented by the image data and the "store" button 1008 has been pressed, the data processing unit 606 determines that an unnecessary region has been defined (YES in step S810), and then advances the processing to step S814. In a case where the user determines that there is no unnecessary region on the image data and does not define an unnecessary region, the data processing unit 606 determines that an unnecessary region has not been defined (NO in step S810), and then advances the processing to step S812.

In step S814, the data processing unit 606 at least reduces pixel values corresponding to the unnecessary region defined in step S807, in other words, the nipple and surrounding region. The data processing unit 606 specifies pixels corresponding to the unnecessary region in image data, and reduces (or attenuates) pixel values of the specified pixels to values as close to zero as possible or reduces the pixel values to zero (in other words, erases the pixel values), thus removing a signal derived from the nipple from the image data.

In step S809, the data processing unit 606 temporarily stores the image data generated in step S814 in a storage unit, such as the data storage unit 608 or a RAM.

In step S811, the data processing unit 606 advances the current slice position from the skin surface toward the inside of the body. Then, the data processing unit 606 selects image data corresponding to a new slice position as a processing target, and then returns the processing to step S805. In this way, each time processing in step S811 is performed, the data processing unit 606 gradually advances the slice position indicated by the image data serving as a processing target from the surface of the body, such as the skin surface, toward the inside of the body.

If, in step S810, it is determined that an unnecessary region has not been defined, the data processing unit 606 determines that an unnecessary region derived from the nipple and surrounding region is not present in the current depth and subsequent depths, and thus does not perform processing for specifying an unnecessary region and erasing pixel values.

In step S812, the data processing unit 606 generates and stores an image obtained by combining, by the maximum intensity projection method, images of all of the slices from a slice of the depth at which it is determined in step S810 that a nipple and surrounding region is not defined to slices of subsequent depths toward the inside of the body. In other words, the data processing unit 606 generates an MIP image using images of all of the slices from a slice of the depth at which a nipple and surrounding region is not defined up to a slice at the largest depth (the deepest portion).

In step S813, the data processing unit 606 generates an image obtained by combining, by the maximum intensity projection method, one or a plurality of pieces of image data generated and temporarily stored in step S809 and one or a plurality of pieces of image data generated and stored in step S812.

In step S815, the data processing unit 606 stores the image data generated in step S813 in the data storage unit 608.

Figure 12A:
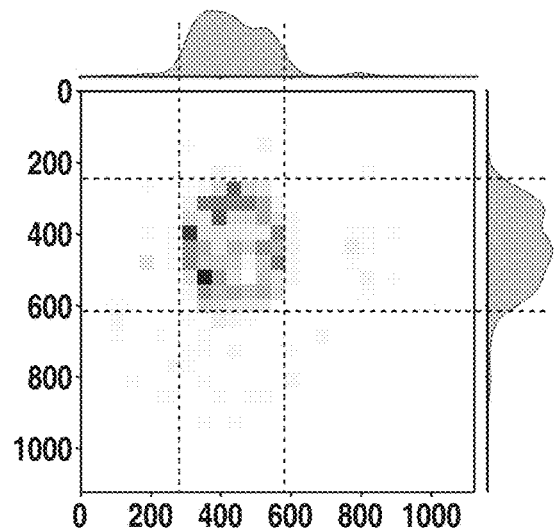
FIGS. 12A, 12B, 12C, and 12D are diagrams illustrating examples of images of distribution densities of feature points.
Figure 12B:
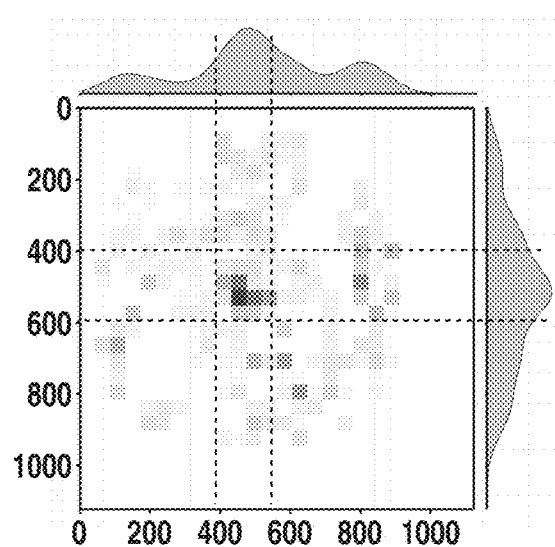
Figure 12C:
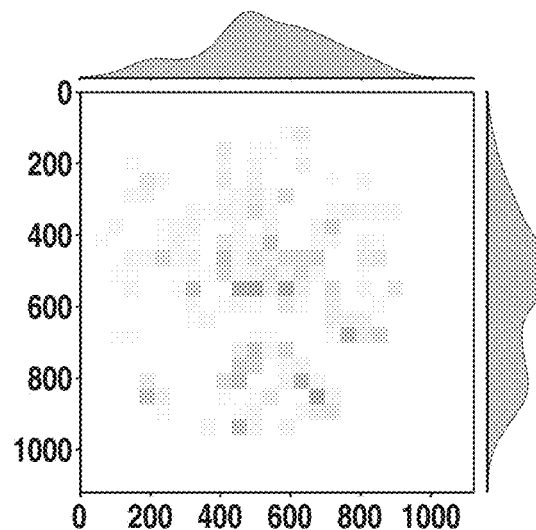
Figure 12D:
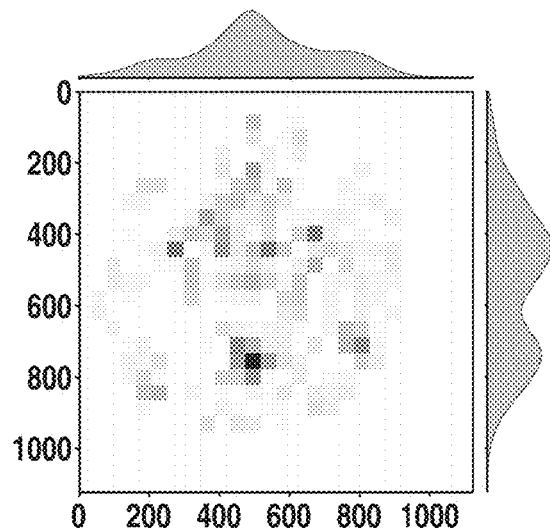

FIGS. 12A, 12B, 12C, and 12D illustrate examples of images each of which is displayed in step S807 and in each of which information about the distribution of feature points is displayed. The images illustrated in FIGS. 12A to 12D are obtained by generating images while sequentially changing the respective depths in the depth direction (a direction from the skin surface toward the inside of the body), performing calculation of respective local feature quantities, and imaging the distribution of feature points. In FIG. 12A, a region having a very high distribution density of feature points is visualized. The user defines this region having a high distribution density of feature points as an unnecessary region and stores an image obtained by reducing pixel values of the defined unnecessary region, and, after that, an image in which a feature quantity image is highlighted illustrated in FIG. 12B is acquired. In the depth image illustrated in FIG. 12C acquired next to the image illustrated in FIG. 12B, there are no portions in which the distribution density of feature points is extremely high, and, therefore, the user presses the "store" button 1008 without setting any unnecessary region. Then, the processing proceeds to step S812. Thus, in the images illustrated in FIGS. 12C and 12D, which are images acquired at the positions deeper than the position of the image illustrated in FIG. 12B, any unnecessary region is not set.

Figure 11A:
FIGS. 11A and 11B are diagrams illustrating examples of an image of a breast generated by the maximum intensity projection method while a signal derived from the nipple and surrounding region is not removed and an image of the breast generated by the maximum intensity projection method after a signal derived from a region defined as an unnecessary region is removed.
Figure 11B:
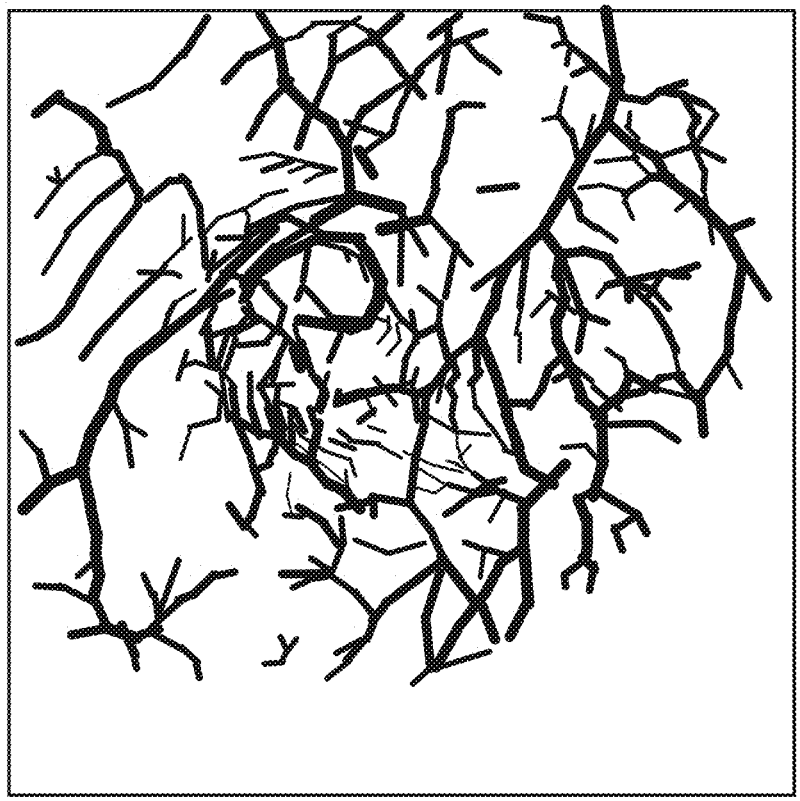

FIG. 11A illustrates a MIP image of the breast generated by the maximum intensity projection method without removal of a signal derived from the nipple and surrounding region. FIG. 11B illustrates a MIP image of the breast generated by the maximum intensity projection method after removal of a signal derived from a region defined as an unnecessary region.

In FIG. 11A, since the intensity of a signal derived from the nipple and its surrounding tissues is strong, it is impossible to observe the structure of blood vessels present in portions closer to the inside of the body than the nipple and its surrounding tissues. According to the present exemplary embodiment, since a signal derived from the nipple and its surrounding tissues can be removed, as illustrated in FIG. 11B, it is possible to observe blood vessels of the nipple and its surrounding tissues.

As illustrated in FIG. 7 and FIG. 11A, in an image generated from volume data acquired by a photoacoustic apparatus, since a strong signal is acquired from the nipple and its surrounding tissues, the nipple and its surrounding tissues become a noise source when being imaged for the purpose of visualizing blood vessels.

With regard to the nipple and its surrounding tissues, a clear boundary thereof is not able to be acquired from an image thereof, it is difficult to mechanically specify and erase such a region.

In particular, since, in a case where imaging is performed on the coronal plane and slices are advanced in the depth direction, regions in which visualization of blood vessels is hindered by a signal derived from the nipple and its surrounding tissues vary for each depth, it is difficult to constantly specify and erase a given region from an image of the surface.

According to the present exemplary embodiment, focusing on feature points of an image and visualizing a distribution thereof enable providing, to the user, a method of easily determining and defining an unnecessary region.

While, in the first exemplary embodiment, an unnecessary region is defined using local feature quantities of an image, a method of defining an unnecessary region using a signal intensity ratio of photoacoustic signals generated due to irradiation with light of a plurality of wavelengths is described as a second exemplary embodiment.

It is known that, as illustrated in FIG. 5, absorption spectra of oxygenated hemoglobin and deoxygenated hemoglobin differ according to wavelengths of light used for irradiation. This effect can be used to obtain an oxygen saturation by radiating light of a plurality of wavelengths and calculating an abundance ratio between oxygenated hemoglobin and deoxygenated hemoglobin.

It is empirically known that, when an oxygen saturation is calculated and imaged based on data about photoacoustic waves generated due to irradiation with light of a plurality of wavelengths, the nipple and its surrounding tissues are imaged as if they are blood vessels with a given oxygen saturation.

For this reason, displaying, as histograms in the region 1002 illustrated in FIG. 10, the frequencies of pixels indicating an oxygen saturation derived and calculated from the nipple and its surrounding tissues enables defining an unnecessary region in a way similar to using a frequency distribution of local feature quantities in the first exemplary embodiment.

As with the first exemplary embodiment, reducing signal values of a region of volume data corresponding to the coordinates of the defined unnecessary region enables acquiring a blood vessel image such as that illustrated in FIG. 11B.

Figure 13:
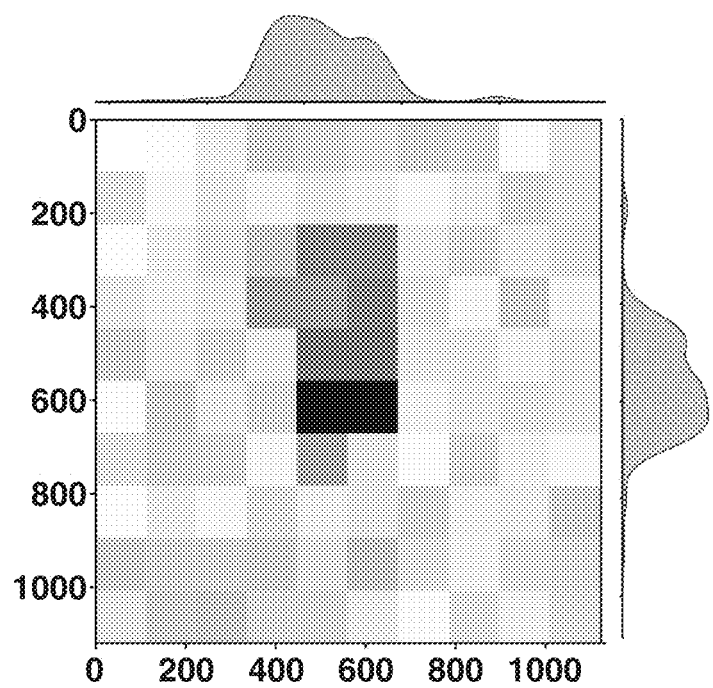
FIG. 13 is a diagram illustrating an example of a distribution of pixels indicating an oxygen saturation equivalent to an oxygen saturation which is specifically observed at a papillary portion.

FIG. 13 illustrates an example of an image indicating a distribution of pixels exhibiting oxygen saturations equivalent to an oxygen saturation that is specifically observed at the papillary portion. As in the feature point distributions employed in the first exemplary embodiment illustrated in, for example, FIGS. 9A to 9C and FIG. 10, the frequency distributions of pixels exhibiting the above oxygen saturations are displayed along the vertical axis and the horizontal axis of the image region.

While referring to the image illustrated in FIG. 13, the user can readily define an unnecessary region.

In the above-described first exemplary embodiment, an example in which a region the range of which is designated by the user is set as an unnecessary region has been described. In a third exemplary embodiment, a configuration of automatically specifying an unnecessary region from image data, without the user performing designation of an unnecessary region, and generating an image with the unnecessary region removed is described.

In the third exemplary embodiment, an example of using a photoacoustic apparatus similar to that in the first exemplary embodiment and removing a signal derived from the nipple is also described.

Figure 14:
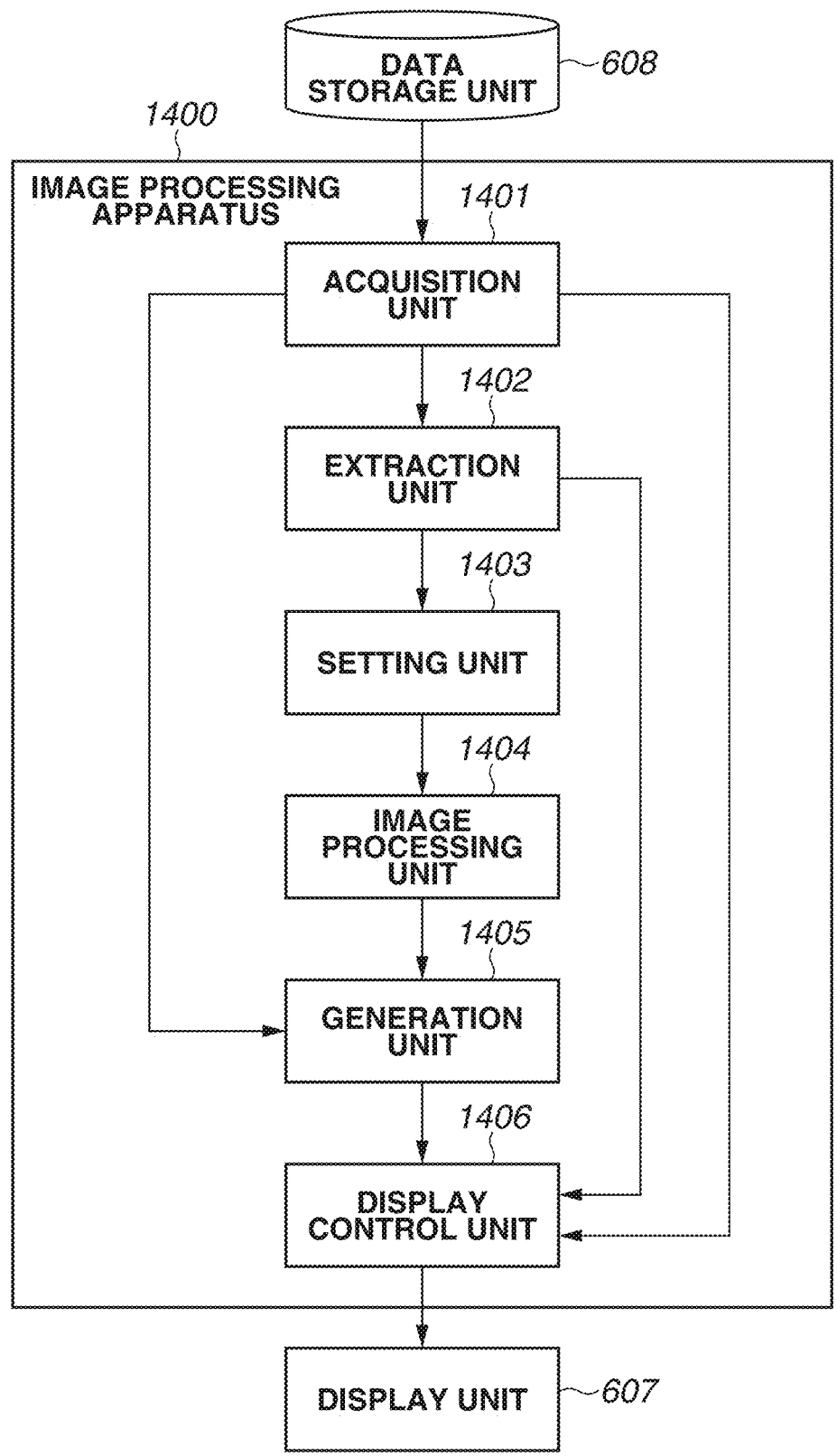
FIG. 14 is a diagram illustrating an example of a functional configuration of an image processing apparatus.

FIG. 14 is a diagram illustrating an example of a functional configuration of an image processing apparatus 1400 according to the third exemplary embodiment. The image processing apparatus 1400 in the present exemplary embodiment is equivalent to the data processing unit 606 in each of the above-described exemplary embodiments. The image processing apparatus 1400 can include the display unit 607 or the data storage unit 608. While not illustrated in FIG. 14, the image processing apparatus 1400 can include other component units illustrated in FIG. 6.

As in the first exemplary embodiment, in the image processing apparatus 1400, a processor, such as a CPU or a GPU, operates in cooperation with a non-transitory storage medium, such as a ROM, a magnetic disc, or a flash memory, and a volatile storage medium, such as a RAM. Thus, each function is implemented by at least one processor executing a program (instructions) stored in at least one memory. The image processing apparatus 1400 can be configured to operate as a "cloud system" (one or a plurality of virtual servers).

The image processing apparatus 1400 in the present exemplary embodiment includes an acquisition unit 1401, an extraction unit 1402, a setting unit 1403, an image processing unit 1404, a generation unit 1405, and a display control unit 1406 as the respective functional units. In implementing the present exemplary embodiment, the display control unit 1406 is not essential. Therefore, outputting to the display control unit 1406 or display control over the display control unit 1406 does not need to be performed.

The acquisition unit 1401 (an acquisition unit) acquires, from the data storage unit 608, a plurality of pieces of first image data generated using volume data that is based on acoustic waves (photoacoustic data in each of the above-described exemplary embodiments). In the present exemplary embodiment, the first image data is also two-dimensional image data that is generated with projection by the maximum intensity projection method, in other words, MIP image data. In a case where no first image data is previously stored in the data storage unit 608, the generation unit 1405, which is described below, generates first image data using volume data. Specifically, as in the above-described exemplary embodiments, the generation unit 1405 generates a plurality of pieces of first image data by changing slice positions of volume data and performing projection with a predetermined slice thickness by the maximum intensity projection method. In the case of removing a signal derived from the nipple, it is desirable that the slice position is gradually moved from the skin surface, which is the body surface, toward the inside of the body. Then, the acquisition unit 1401 outputs the acquired plurality of pieces of first image data to the extraction unit 1402, the generation unit 1405, and the display control unit 1406.

The extraction unit 1402 (an extraction unit) receives a plurality of pieces of first image data output from the acquisition unit 1401 and extracts feature points from the plurality of pieces of first image data. More specifically, the extraction unit 1402 performs processing such as that illustrated in FIG. 3 on each piece of image data of the plurality of pieces of first image data, and extracts feature points having local feature quantities from each piece of image data. The method of extracting feature points is not limited to the above-mentioned method. The extraction unit 1402 outputs information about the extracted feature points and the plurality of pieces of first image data to the setting unit 1403. The extraction unit 1402 outputs information about the extracted feature points to the display control unit 1406.

The setting unit 1403 (a setting unit) receives the information about the extracted feature points and the plurality of pieces of first image data output from the extraction unit 1402. Then, the setting unit 1403 sets an unnecessary region to one or a plurality of pieces of first image data using a distribution of the extracted feature points. Specifically, the setting unit 1403 obtains a distribution density of feature points with respect to each piece of received first image data. As described above, a region having a high distribution density of feature points is likely to be a nipple and surrounding region (in other words, an unnecessary region). Therefore, the setting unit 1403 determines the presence or absence of such a region with respect to each piece of first image data. If a region having a distribution density higher than a predetermined value is included in image data, the setting unit 1403 determines that the image data is image data including an unnecessary region. If not, the setting unit 1403 determines that the image data is image data including no unnecessary region. The predetermined value serving as a criterion for determination can be set to any optional value. With respect to one or a plurality of pieces of first image data determined to be image data including an unnecessary region, the setting unit 1403 sets pixels of a region determined to have a high distribution density of feature points as pixels of an unnecessary region. The setting unit 1403 outputs information about the set pixels (for example, the coordinates of pixels) and one or a plurality of pieces of first image data including an unnecessary region to the image processing unit 1404.

The image processing unit 1404 (an image processing unit) receives information about pixels set as an unnecessary region and one or a plurality of pieces of first image data including an unnecessary region output from the setting unit 1403. Then, with respect to one or a plurality of pieces of first image data in which an unnecessary region is set, the image processing unit 1404 at least reduces pixel values of the unnecessary region. With respect to each piece of image data determined to include an unnecessary region, the image processing unit 1404 specifies pixels the pixel values of which to reduce, based on information about the pixels set as an unnecessary region. Then, the image processing unit 1404 at least reduces pixel values of the specified pixels, thus removing an unnecessary region from each piece of image data. The image processing unit 1404 outputs one or a plurality of pieces of first image data from which an unnecessary region has been removed to the generation unit 1405.

The generation unit 1405 (a generation unit) receives one or a plurality of pieces of first image data from which an unnecessary region has been removed, output from the image processing unit 1404. The generation unit 1405 receives a plurality of pieces of first image data output from the acquisition unit 1401. Then, the generation unit 1405 generates second image data using one or a plurality of pieces of first image data in which the pixel values of an unnecessary region have at least been reduced and one or a plurality of pieces of first image data in which no unnecessary region is included. Specifically, first, the generation unit 1405 acquires one or a plurality of pieces of first image data from which an unnecessary region has been removed, output from the image processing unit 1404. Then, with respect to a plurality of pieces of first image data output from the acquisition unit 1401, the generation unit 1405 acquires one or a plurality of pieces of first image data in which no unnecessary region is included. The generation unit 1405 performs integration and projection of these pieces of first image data by the maximum intensity projection method, thus generating one or a plurality of MIP images as second image data. Then, the generation unit 1405 outputs the generated second image data to the display control unit 1406.

The display control unit 1406 (a display control unit) receives one or a plurality of pieces of first image data output from the acquisition unit 1401. The display control unit 1406 receives information about feature points output from the extraction unit 1402. Then, the display control unit 1406 causes the display unit 607 to display an image represented by the received one or a plurality of pieces of first image data and the received information about feature points. As in the first exemplary embodiment, these pieces of information can be displayed on a GUI such as that illustrated in FIG. 10. In this way, the user can confirm the distribution of feature points in each piece of image data. The setting unit 1403 can receive, from the user, the designation of one point on the displayed image and then set this point as a reference point used in the first exemplary embodiment. The image processing unit 1404 can set an unnecessary region using this reference point and the distribution of feature points. With this configuration employed, in automatically setting the nipple and its surrounding region as an unnecessary region, if the nipple position is set as a reference point, such a region can be distinguished from another location having many local feature quantities derived from, for example, body hair or a mole on the body surface. In other words, an unnecessary region can be set with high accuracy.

The display control unit 1406 receives the second image data output from the generation unit 1405, and causes the display unit 607 to display the received second image data. In this way, the user can confirm the result of such a series of processing operations.

Next, a processing procedure in the third exemplary embodiment is described with reference to the flowchart illustrated in FIG. 15. The content or order of each step illustrated in FIG. 15 is merely an example, and can be modified in various manners according to intended uses or purposes.

In step S1501, the acquisition unit 1401 acquires a plurality of pieces of first image data from the data storage unit 608. As described above, the plurality of pieces of first image data is MIP image data generated using volume data that is based on acoustic waves (photoacoustic data).

In step S1502, the extraction unit 1402 extracts feature points from each piece of the plurality of pieces of first image data acquired in step S1501. The method of extracting feature points, which includes the method illustrated in FIG. 3 or a known method, is used to extract feature points having local feature quantities that are robust over enlargement, reduction, rotation, and luminance change.

In step S1503, the display control unit 1406 causes the display unit 607 to display a plurality of pieces of first image data acquired in step S1501 and information about feature points acquired in step S1502. Step S1503 enables the user to designate a reference point, and is, therefore, not essential to the present processing. The display control unit 1406 performs displaying of a screen such as that illustrated in FIG. 10 described above. The screen is displayed so as to include both any piece of first image data and information about feature points corresponding to the displayed first image data (for example, feature points themselves, two-dimensional histograms, and image data having the estimated density of feature points). Then, the setting unit 1403 receives the designation of a reference point with respect to at least one piece of first image data.

In step S1504, the setting unit 1403 sets an unnecessary region to one or a plurality of pieces of first image data using the distribution of feature points extracted in step S1502. As described above, the setting unit 1403 obtains a distribution density of feature points with respect to each piece of image data, and sets a region having a distribution density higher than a predetermined value as an unnecessary region. In a case where the designation of a reference point is previously received in step S1503, the setting unit 1403 only needs to determine whether the distribution density around the reference point is higher than the predetermined value.

In step S1505, with respect to one or a plurality of pieces of first image data in which an unnecessary region is included, the image processing unit 1404 at least reduces pixel values of the pixels set as an unnecessary region in step S1504. The image processing unit 1404 specifies pixels equivalent to the unnecessary region in image data, and reduces (or attenuates) pixel values of the specified pixels to values as close to zero as possible or reduces the pixel values to zero (in other words, erases the pixel values), thus removing a signal derived from the nipple from the image data. If it becomes difficult to view an unnecessary region in second image data generated in step S1506 described below, any image processing operation can be performed.

In step S1506, the generation unit 1405 generates second image data using one or a plurality of pieces of first image data in which pixel values of the unnecessary region have at least been reduced and one or a plurality of pieces of first image data in which no unnecessary region is included. The generation unit 1405 combines these pieces of image data by the maximum intensity projection method, thus generating MIP image data as second image data. An example of the second image data generated in this way is illustrated in FIG. 11B, which is described in the first exemplary embodiment.

In step S1507, the display control unit 1406 causes the display unit 607 to display the second image data generated in step S1506. With this, the user can confirm the result of image generation.

The above-described configuration enables solving the issue that it is difficult to discriminate between a photoacoustic signal derived from the vicinity of the nipple and areola and a photoacoustic signal derived from a region of interest which is present closer to the inside of the body than the nipple and areola.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random access memory (RAM), a read-only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-228149, filed Nov. 28, 2017, which is hereby incorporated by reference herein in its entirety.

What is claimed is:

1. An image processing apparatus comprising:
a memory storing a program; and
one or more processors which, by executing the program, function as:
an acquisition unit configured to acquire a plurality of pieces of first image data that are based on acoustic waves corresponding, respectively, to a plurality of positions in a subject;
an extraction unit configured to extract feature points from the plurality of pieces of the first image data corresponding, respectively, to the plurality of positions in the subject;
a setting unit configured to set an unnecessary region to first pieces of the first image data in the acquired plurality of pieces of the first image data, using a distribution of the extracted feature points;
an image processing unit configured to modify the first pieces of the first image data in the acquired plurality of pieces of the first image data, to which the unnecessary region has been set, by reducing pixel values of the unnecessary region in the first pieces of the first image data in the acquired plurality of pieces of the first image data, to which the unnecessary region has been set; and
a generation unit configured to generate second image data using (i) the modified first pieces of the first image data, in which the pixel values of the unnecessary region have been reduced, and (ii) second pieces of the first image data in the acquired plurality of pieces of the first image data, in which the unnecessary region is not included, the second pieces of the first image data being different from the first pieces of the first image data.

2. The image processing apparatus according to claim 1, wherein the setting unit sets a reference point in at least one piece of the first image data, and sets the unnecessary region using the reference point and the distribution of the extracted feature points.

3. The image processing apparatus according to claim 1, wherein the one or more processors, by executing the program, further function as a display control unit configured to cause a display unit to display an image represented by the first image data and information about the feature points included in the first image data, and
wherein the setting unit sets a point designated on the displayed image as a reference point.

4. The image processing apparatus according to claim 3, wherein the information about the feature points is a two-dimensional histogram indicating a distribution of the feature points.

5. The image processing apparatus according to claim 3, wherein the information about the feature points is an image having an estimated density of the feature points.

6. The image processing apparatus according to claim 3, wherein the display control unit further causes the display unit to display a graphical user interface for switching one piece of the first image data that is being displayed to another piece of the first image data.

7. The image processing apparatus according to claim 1, wherein the generation unit generates the second image data by a maximum intensity projection method.

8. The image processing apparatus according to claim 1, wherein the generation unit generates the second image data by combining the modified first pieces of the first image data in which the pixel values of the unnecessary region have been reduced and the second pieces of the first image data in which the unnecessary region is not included.

9. The image processing apparatus according to claim 1, wherein volume data is data acquired by performing photoacoustic measurement with respect to a breast of a subject, and wherein the unnecessary region is a region equivalent to a nipple and surrounding region of the breast.

10. The image processing apparatus according to claim 1, wherein the setting unit sets the unnecessary region to each piece of first image data, and the image processing unit removes the unnecessary region from each piece of first image data.

11. An image processing method comprising:
acquiring a plurality of pieces of first image data that are based on acoustic waves corresponding, respectively, to a plurality of positions in a subject;
extracting feature points from the acquired plurality of pieces of the first image data corresponding, respectively, to the plurality of positions in the subject;
setting an unnecessary region to first pieces of the first image data in the acquired plurality of pieces of the first image data, using a distribution of the extracted feature points;
modifying the first pieces of the first image data in the acquired plurality of pieces of the first image data, to which the unnecessary region has been set, by reducing pixel values of the unnecessary region in the first pieces of the first image data in the acquired plurality of pieces of the first image data, to which the unnecessary region has been set; and generating second image data using (i) the modified first pieces of the first image data, in which the pixel values of the unnecessary region have been reduced, and (ii) second pieces of the first image data in the acquired plurality of pieces of the first image data, in which the unnecessary region is not included, the second pieces of the first image data being different from the first pieces of the first image data.

12. A non-transitory computer-readable storage medium storing computer-executable instructions that, when executed by a computer, cause the computer to perform a process comprising:

acquiring a plurality of pieces of first image data that are based on acoustic waves corresponding, respectively, to a plurality of positions in a subject;

extracting feature points from the acquired plurality of pieces of the first image data corresponding, respectively, to the plurality of positions in the subject;

setting an unnecessary region to first pieces of the first image data in the acquired plurality of pieces of the first image data, using a distribution of the extracted feature points;

modifying the first pieces of the first image data in the acquired plurality of pieces of the first image data, to which the unnecessary region has been set, by reducing pixel values of the unnecessary region in the first pieces of the first image data in the acquired plurality of pieces of the first image data, to which the unnecessary region has been set; and generating second image data using (i) the modified first pieces of the first image data, in which the pixel values of the unnecessary region have been reduced, and (ii) second pieces of the first image data in the acquired plurality of pieces of the first image data, in which the unnecessary region is not included, the second pieces of the first image data being different from the first pieces of the first image data.

* * * * *